US012678339B2

(12) United States Patent (10) Patent No.: US 12,678,339 B2
Simmons (45) Date of Patent: Jul. 14, 2026

(54) TISSUE INTERFACE FOR TISSUE DEBRIDEMENT

(71) Applicant: KCI Manufacturing Unlimited Company, Athlone (IE)

(72) Inventor: Tyler H. Simmons, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 623 days.

(21) Appl. No.: 18/015,260

(22) PCT Filed: Jun. 14, 2021

(86) PCT No.: PCT/IB2021/055229

§ 371 (c)(1),
(2) Date: Jan. 9, 2023

(87) PCT Pub. No.: WO2022/008999

PCT Pub. Date: Jan. 13, 2022

(65) Prior Publication Data

US 2023/0263666 A1 Aug. 24, 2023

Related U.S. Application Data

(60) Provisional application No. 63/049,884, filed on Jul. 9, 2020.

(51) Int. Cl.
A61F 13/05 (2024.01)
A61F 13/00 (2024.01)
(Continued)

(52) U.S. Cl.
CPC ........ A61F 13/05 (2024.01); A61F 13/00995 (2013.01); A61F 13/01025 (2024.01); A61F 2013/00255 (2013.01); A61M 1/915 (2021.05)

(58) Field of Classification Search
CPC ............... A61F 13/05; A61F 13/00995; A61F 13/01025; A61F 2013/00255; A61M 1/915
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/IB2021/055229, mailed Oct. 1, 2021.
(Continued)

*Primary Examiner* — Jessica Arble

(57) ABSTRACT

Dressings, systems and methods of treating a tissue site are described. A method of manufacturing the dressing can include providing a dressing material. The dressing material can have a surface configured to contact the tissue site. The dressing material can also have a plurality of pores. The method can further include applying a compressive force to the dressing material at an angle to the surface, the compressive force causing permanent deformation of the plurality of pores. Causing permanent deformation of the plurality of pores can comprise forming a plurality of compressed pores. Forming a plurality of compressed pores can include compressing the plurality of pores from a generally circular shape to a generally ovular shape.

28 Claims, 8 Drawing Sheets

(51) Int. Cl.
  *A61F 13/01*  (2024.01)
  *A61M 1/00*  (2006.01)

(56)  References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2013/0211310 A1* | 8/2013 | Bommarito | B08B 17/06 428/141 |
| 2013/0211349 A1* | 8/2013 | Stokes | A61L 15/425 604/290 |
| 2014/0163491 A1 | 6/2014 | Schuessler et al. | |
| 2015/0080788 A1 | 3/2015 | Blott et al. | |
| 2015/0320603 A1* | 11/2015 | Locke | A61L 31/146 604/543 |
| 2019/0343687 A1 | 11/2019 | Locke et al. | |
| 2020/0046567 A1 | 2/2020 | Carroll et al. | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |

(56) References Cited

FOREIGN PATENT DOCUMENTS

| | | |
|---|---|---|
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2013116552 A1 | 8/2013 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, Nj, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

TISSUE INTERFACE FOR TISSUE DEBRIDEMENT

CROSS-REFERENCE TO RELATED APPLICATIONS

This application claims the benefit of priority to U.S. Provisional Application No. 63/049,884, filed on Jul. 9, 2020, which is incorporated herein by reference in its entirety.

TECHNICAL FIELD

The invention set forth in the appended claims relates generally to tissue treatment systems and more particularly, but without limitation, to dressing for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a method of manufacturing a dressing for treating a tissue site is described. The method can include providing a dressing material. The dressing material can have a surface configured to contact the tissue site. The dressing material can also have a plurality of pores. The method can further include applying a compressive force to the dressing material at an angle to the surface, the compressive force causing permanent deformation of the plurality of pores. In some embodiments, causing permanent deformation of the plurality of pores can comprise forming a plurality of compressed pores. Forming a plurality of compressed pores can include compressing the plurality of pores from a generally circular shape to a generally ovular shape. In some embodiments, the method may further include orienting a major axis of the ovular-shaped pores perpendicular to the surface.

More generally, a dressing for treating a tissue site is described. The dressing can include a first surface configured to face the tissue site, a second surface opposite the first surface, a thickness extending from the first surface to the second surface, and a plurality of pores having an elliptical shape. The plurality of pores can have a major axis oriented perpendicular to the first surface and the second surface.

Alternatively, other example embodiments may describe a system for providing negative-pressure therapy to a tissue site. The system can include a tissue interface, a sealing member configured to be disposed over the tissue interface to create a sealed space, and a negative pressure source fluidly coupled to the sealed space. The tissue interface can include a first surface configured to face the tissue site, a second surface opposite the first surface, a thickness extending from the first surface to the second surface, and a plurality of pores. Each of the plurality of pores can have an ovoid shape oriented at an angle to the first surface. In some embodiments, the angle can be about 90°. The plurality of pores can be configured to contract in a direction parallel to the first surface and the second surface.

A tissue interface for treating a tissue site, is also described herein, wherein the tissue interface can be formed by a process including providing a dressing material and applying a compressive force to the dressing material. The dressing material can have a surface configured to contact the tissue site and a plurality of pores. The compressive force can be applied to the dressing material at an angle to the surface. The compressive force can also cause permanent deformation of the plurality of pores.

A method for treating a tissue site with negative pressure is also described herein. In some example embodiments, the method can include applying a tissue interface to the tissue site. The tissue interface can include a first surface configured to face the tissue site, a second surface opposite the first surface, a thickness extending from the first surface to the second surface, and a plurality of pores. The plurality of pores can have an elliptical shape and a major axis oriented perpendicular to the first surface and the second surface. The method can further include covering the tissue interface with a cover to form a sealed space containing the tissue interface, fluidly coupling a fluid conductor to the tissue interface, fluidly coupling a negative-pressure source to the fluid conductor, applying negative pressure from the negative-pressure source to the tissue interface through the fluid conductor, and contracting the tissue interface from a first width to a second width in response to an application of negative pressure to the tissue interface. The second width can be less than the first width. In some embodiments, the plurality of pores can be configured to contract in a direction parallel to the first surface and the second surface.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
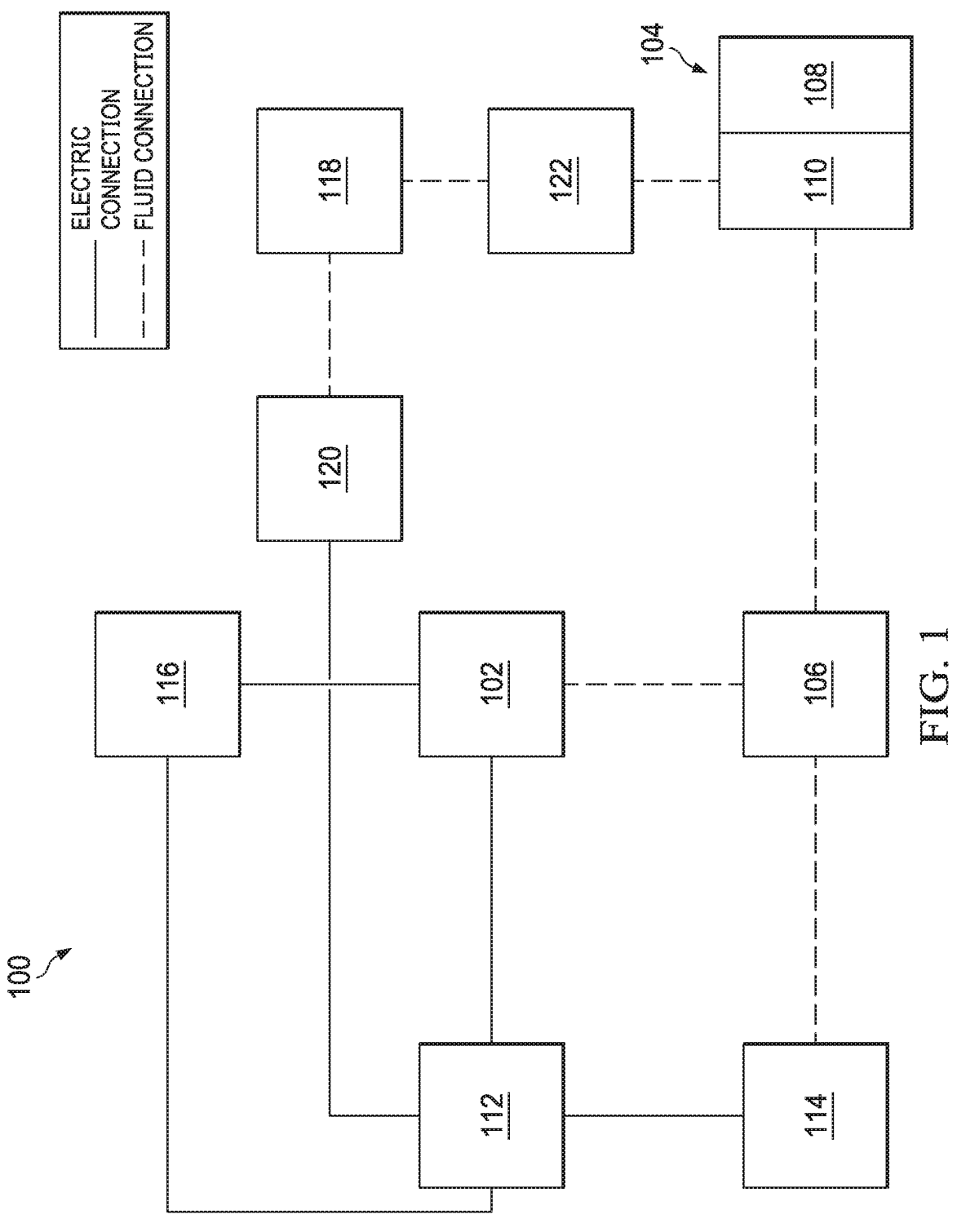
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. As illustrated in the example of FIG. 1, the dressing 104 may comprise or consist essentially of a tissue interface 108, a cover 110, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Texas.

The therapy system 100 may also include a regulator or controller, such as a controller 112. Additionally, the therapy system 100 may include sensors to measure operating parameters and provide feedback signals to the controller 112 indicative of the operating parameters. As illustrated in FIG. 1, for example, the therapy system 100 may include a first sensor 114 and a second sensor 116 coupled to the controller 112.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as a positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 112 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the controller 112, the solution source 118, and other components into a therapy unit.

In general, components of the therapy system 100 may be coupled directly or indirectly. For example, the negative-pressure source 102 may be directly coupled to the container 106 and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 112 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 102, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 102 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. In some embodiments, the container 106 may comprise a canister having a collection chamber, a first inlet fluidly coupled to the collection chamber and a first outlet fluidly coupled to the collection chamber and adapted to receive negative pressure from a source of negative pressure.

The tissue interface 108 can be generally adapted to partially or fully contact a tissue site. The tissue interface 108 may take many forms, and may have many sizes, shapes, or thicknesses, depending on a variety of factors, such as the type of treatment being implemented or the nature and size of a tissue site. The tissue interface 108 may further promote granulation at a tissue site when pressure within the sealed therapeutic environment is reduced. For example, the size and shape of the tissue interface 108 may be adapted to the contours of deep and irregular shaped tissue sites. Any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may comprise or consist essentially of a manifold. A manifold in this context may comprise or consist essentially of a means for collecting or distributing fluid across the tissue interface 108 under pressure. For example, a manifold may be adapted to receive negative pressure from a source and distribute negative pressure through multiple apertures across the tissue interface 108, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 110 may provide a bacterial barrier and protection from physical trauma. The cover 110 may also be constructed from a material that can reduce evaporative losses and provide a fluid seal between two components or two environments, such as between a therapeutic environment and a local external environment. The cover 110 may comprise or consist of, for example, an elastomeric film or membrane that can provide a seal adequate to maintain a negative pressure at a tissue site for a given negative-pressure source. The cover 110 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 110 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 110 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 110 may comprise INSPIRE 2301 having an MVTR (upright cup technique) of 2600 g/m²/24 hours and a thickness of about 30 microns.

An attachment device may be used to attach the cover 110 to an attachment surface, such as undamaged epidermis, a gasket, or another cover. The attachment device may take many forms. For example, an attachment device may be a medically-acceptable, pressure-sensitive adhesive configured to bond the cover 110 to epidermis around a tissue site. In some embodiments, for example, some or all of the cover 110 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. If the tissue site is a wound, for example, the tissue interface 108 may partially or completely fill the wound, or it may be placed over the wound. The cover 110 may be placed over the tissue interface 108 and sealed to an attachment surface near a tissue site. For example, the cover 110 may be sealed to undamaged epidermis peripheral to a tissue site. Thus, the dressing 104 can provide a sealed therapeutic environment proximate to a tissue site, substantially isolated from the external environment, and the negative-pressure source 102 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 108 in the sealed therapeutic environment can induce macro-strain and micro-strain in the tissue site. Negative pressure can also remove exudate and other fluid from a tissue site, which can be collected in container 106.

A controller, such as the controller 112, may be a microprocessor or computer programmed to operate one or more components of the therapy system 100, such as the negative-pressure source 102. In some embodiments, for example, the controller 112 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 108, for example. The controller 112 is also preferably configured to receive one or more input signals, such as a feedback signal, and programmed to modify one or more operating parameters based on the input signals.

Sensors, such as the first sensor 114 and the second sensor 116, are generally known in the art as any apparatus operable to detect or measure a physical phenomenon or property, and generally provide a signal indicative of the phenomenon or property that is detected or measured. For example, the first sensor 114 and the second sensor 116 may be configured to measure one or more operating parameters of the therapy system 100. In some embodiments, the first sensor 114 may be a transducer configured to measure pressure in a pneumatic pathway and convert the measurement to a signal indicative of the pressure measured. In some embodiments, for example, the first sensor 114 may be a piezo-resistive strain gauge. The second sensor 116 may optionally measure operating parameters of the negative-pressure source 102, such as a voltage or current, in some embodiments. Preferably, the signals from the first sensor 114 and the second sensor 116 are suitable as an input signal to the controller 112, but some signal conditioning may be appropriate in some embodiments. For example, the signal may need to be filtered or amplified before it can be processed by the controller 112. Typically, the signal is an electrical signal, but may be represented in other forms, such as an optical signal.

In some embodiments, the controller 112 may receive and process data from one or more sensors, such as the first sensor 114. The controller 112 may also control the operation of one or more components of the therapy system 100 to manage the pressure delivered to the tissue interface 108. In some embodiments, controller 112 may include an input for receiving a desired target pressure and may be programmed for processing data relating to the setting and inputting of the target pressure to be applied to the tissue interface 108. In some example embodiments, the target pressure may be a fixed pressure value set by an operator as the target negative pressure desired for therapy at a tissue site and then provided as input to the controller 112. The target pressure may vary from tissue site to tissue site based on the type of tissue forming a tissue site, the type of injury or wound (if any), the medical condition of the patient, and the preference of the attending physician. After selecting a desired target pressure, the controller 112 can operate the negative-pressure source 102 in one or more control modes based on the target pressure and may receive feedback from one or more sensors to maintain the target pressure at the tissue interface 108.

During treatment of a tissue site, some tissue sites may not heal according to the normal medical protocol and may develop areas of necrotic tissue. Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include a viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax. Eschar may be difficult to remove without the use of surgical cutting instruments.

In addition to necrotic tissue, slough, and eschar, the tissue site may include biofilms, lacerated tissue, devitalized tissue, contaminated tissue, damaged tissue, infected tissue, exudate, highly viscous exudate, fibrinous slough and/or other material that can generally be referred to as debris. The debris may inhibit the efficacy of tissue treatment and slow the healing of the tissue site. If the debris is in the tissue site, the tissue site may be treated with different processes to disrupt the debris. Examples of disruption can include softening of the debris, separation of the debris from desired tissue, such as the subcutaneous tissue, preparation of the debris for removal from the tissue site, and removal of the debris from the tissue site.

The debris can require debridement performed in an operating room. In some cases, tissue sites requiring debridement may not be life-threatening, and debridement may be considered low-priority. Low-priority cases can experience delays prior to treatment as other, more life-threatening, cases may be given priority for an operating room. As a result, low priority cases may need temporization. Temporization can include stasis of a tissue site that limits deterioration of the tissue site prior to other treatments, such as debridement, negative-pressure therapy or instillation.

When debriding, clinicians may find it difficult to define separation between healthy, vital tissue and necrotic tissue. As a result, normal debridement techniques may remove too much healthy tissue or not enough necrotic tissue. If non-viable tissue demarcation does not extend deeper than the deep dermal layer, or if the tissue site is covered by the debris, such as slough or fibrin, gentle methods to remove the debris should be considered to avoid excess damage to the tissue site.

In some debridement processes, a mechanical process is used to remove the debris. Mechanical processes may include using scalpels or other cutting tools having a sharp edge to cut away the debris from the tissue site. Other mechanical processes may use devices that can provide a stream of particles to impact the debris to remove the debris in an abrasion process, or jets of high pressure fluid to impact the debris to remove the debris using water-jet cutting or lavage. Typically, mechanical processes of debriding a tissue site may be painful and may require the application of local anesthetics. Mechanical processes also risk over removal of healthy tissue that can cause further damage to the tissue site and delay the healing process.

Debridement may also be performed with an autolytic process. For example, an autolytic process may involve using enzymes and moisture produced by a tissue site to soften and liquefy the necrotic tissue and debris. Typically, a dressing may be placed over a tissue site having debris so that fluid produced by the tissue site may remain in place, hydrating the debris. Autolytic processes can be pain-free, but autolytic processes are a slow and can take many days. Because autolytic processes are slow, autolytic processes may also involve many dressing changes. Some autolytic processes may be paired with negative-pressure therapy so that, as debris hydrates, negative pressure supplied to a tissue site may draw off the debris. In some cases, a manifold positioned at a tissue site to distribute negative-pressure across the tissue site may become blocked or clogged with debris broken down by an autolytic process. If a manifold becomes clogged, negative-pressure may not be able to remove debris, which can slow or stop the autolytic process.

Debridement may also be performed by adding enzymes or other agents to the tissue site that digest tissue. Often, strict control of the placement of the enzymes and the length of time the enzymes are in contact with a tissue site must be maintained. If enzymes are left on a tissue site for longer than needed, the enzymes may remove too much healthy tissue, contaminate the tissue site, or be carried to other areas of a patient. Once carried to other areas of a patient, the enzymes may break down undamaged tissue and cause other complications.

Furthermore, some dressings for treating a tissue site may comprise a tissue interface configured to mechanically debride slough and loosen tissue. The tissue interface may rely primarily on mechanical action in a single direction or along one primary axis. For example, the tissue interface may collapse vertically into the wound and provide only some lateral movement to debride the tissue site under negative pressure. While a tissue interface having mechanical action along a primary axis can provide beneficial debridement treatment, there is a desire to further increase the effectiveness of the tissue interface for debridement treatment.

These limitations and others may be addressed by the therapy system 100, which can provide negative-pressure therapy, instillation therapy, and disruption of debris. In some embodiments, the therapy system 100 can provide mechanical movement at a surface of the tissue site in combination with cyclic delivery and dwell of topical solutions to help solubilize debris. For example, a negative-pressure source may be fluidly coupled to a tissue site to provide negative pressure to the tissue site for negative-pressure therapy. In some embodiments, a fluid source may be fluidly coupled to a tissue site to provide therapeutic fluid to the tissue site for instillation therapy. In some embodiments, the therapy system may include a tissue interface comprised of a felted foam and having a plurality of ovular-shaped pores. The ovular-shaped pores may be preferentially aligned within the tissue interface. For example, the ovular-shaped pores may be aligned within the tissue interface so that when the tissue interface is positioned at a tissue site, the ovular-shaped pores resist vertical compression under negative pressure and are susceptible to horizontal compression. The ovular-shaped pores may enable the tissue interface to collapse in the horizontal direction to provide a second axis of mechanical action to disrupt debris at the tissue site. Following the disruption of the debris, negative-pressure therapy, instillation therapy, and other processes may be used to remove the debris from the tissue site. In some embodiments, the therapy system 100 may be used in conjunction with other tissue removal and debridement techniques. For example, the therapy system 100 may be used prior to enzymatic debridement to soften the debris. In another example, other mechanical debridement may be used to remove a portion of the debris at the tissue site, and the therapy system 100 may then be used to remove the remaining debris while reducing the risk of trauma to the tissue site.

Figure 2:
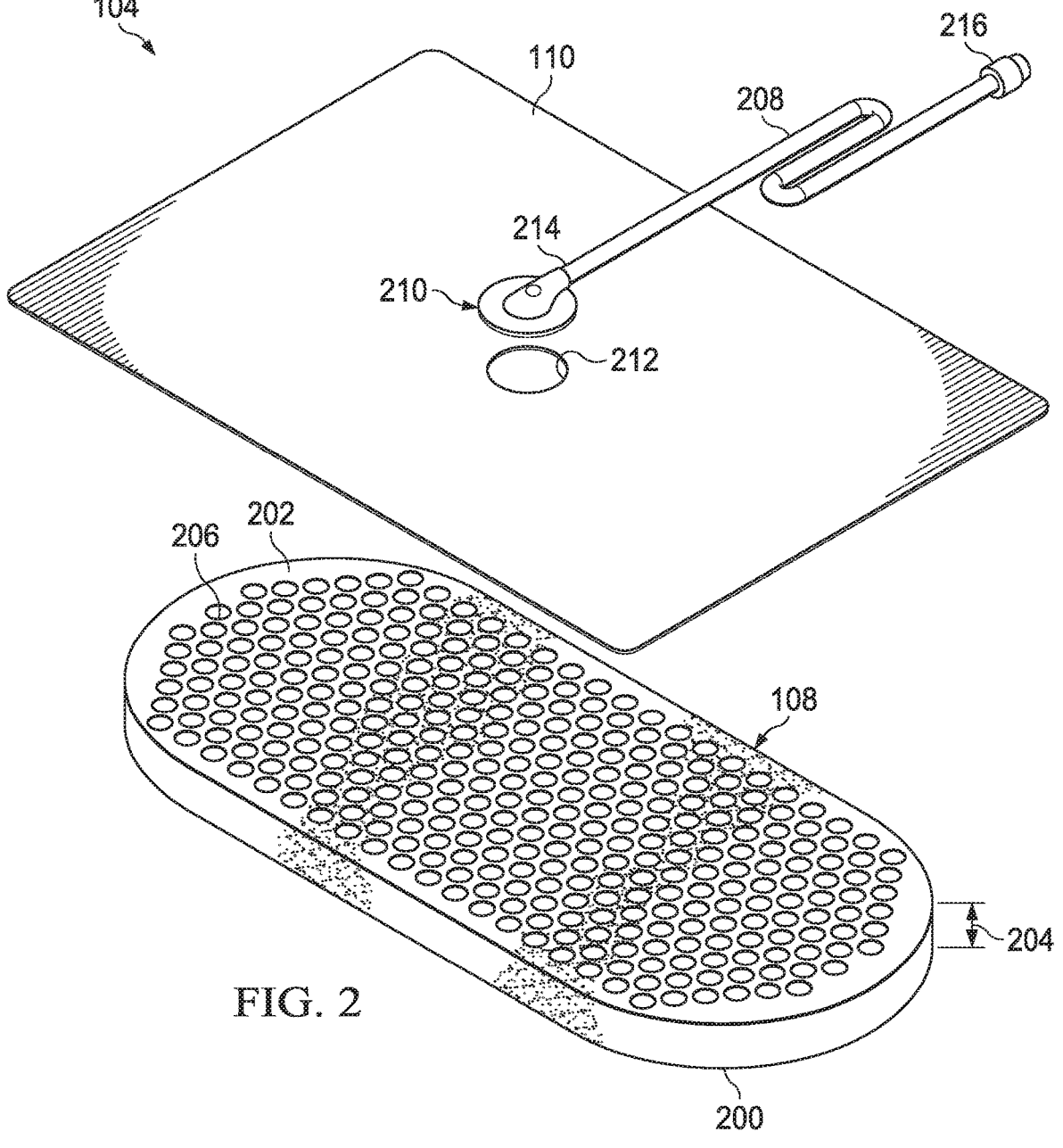
FIG. 2 is an assembly view of an example of a dressing of FIG. 1, illustrating additional details that may be associated with some embodiments.

FIG. 2 is an assembly view of an example of the dressing 104 of FIG. 1, illustrating additional details that may be associated with some embodiments. In some embodiments, the dressing 104 may comprise the tissue interface 108. The tissue interface 108 may have a first surface 200 and a second surface 202. The first surface 200 may configured to face a tissue site. The second surface 202 may be opposite the first surface 200. The tissue interface 108 may have a substantially uniform thickness 204 extending from the first surface 200 to the second surface 202. In some embodiments, the thickness 204 may be between about 5 mm and about 15 mm. In other embodiments, the thickness 204 may be thinner or thicker than the stated range as needed for the particular application of the dressing 104. In some embodiments, the tissue interface 108 may have a plurality of apertures or holes, such as a plurality of holes 206, extending into the tissue interface 108 from the first surface 200 toward the second surface 202.

In some embodiments, the dressing 104 may include a fluid conductor 208 and a fluid port, such as a dressing interface 210. In some embodiments, the fluid conductor 208 may be a flexible tube. In some embodiments, the fluid conductor may comprise a first end 214 and a second end 216. The first end 214 of the fluid conductor 208 may be configured to be fluidly coupled to the dressing interface 210 and the second end 216 of the fluid conductor 208 may be configured to be fluidly coupled to the negative-pressure source 102 (not shown).

In some embodiments, the dressing interface 210 may be an elbow connector, as shown in the example of FIG. 2, which can be coupled to the cover 110 and fluidly coupled to the tissue interface 108. In some embodiments, the dressing interface 210 may be placed over an aperture 212 in the cover 110 to provide a fluid path between the fluid conductor 208 and the tissue interface 108. In other embodiments, the first end 214 of the fluid conductor 208 may be inserted directly through the cover 110 into the tissue interface 108. The cover 110 may be configured to be disposed over the tissue interface 108 to create a sealed space. In some embodiments, the cover 110 may be configured to be disposed over the second surface 202 of the tissue interface 108. In some embodiments, the cover 110 may include the aperture 212. In other embodiments, the aperture 212 may be cut into the cover 110 before or after positioning the cover 110 over the tissue interface 108. In some embodiments, the aperture 212 may be centrally disposed in the cover 110. In other embodiments, the position of the aperture 212 may be off-center or adjacent to an end or edge of the cover 110.

In some embodiments, the tissue interface 108 may be provided as a portion of an assembly or kit for forming the dressing 104. In other embodiments, the tissue interface 108 may be provided separately from the cover 110, the fluid conductor 208, and the dressing interface 210 for assembly of the dressing 104 at the point of use.

If not already configured, the dressing interface 210 may be disposed over the aperture 212 and attached to the cover 110. The first end 214 of the fluid conductor 208 may be fluidly coupled to the dressing interface 210 and the second end 216 of the fluid conductor 208 may be fluidly coupled to the negative-pressure source 102.

Figure 3:
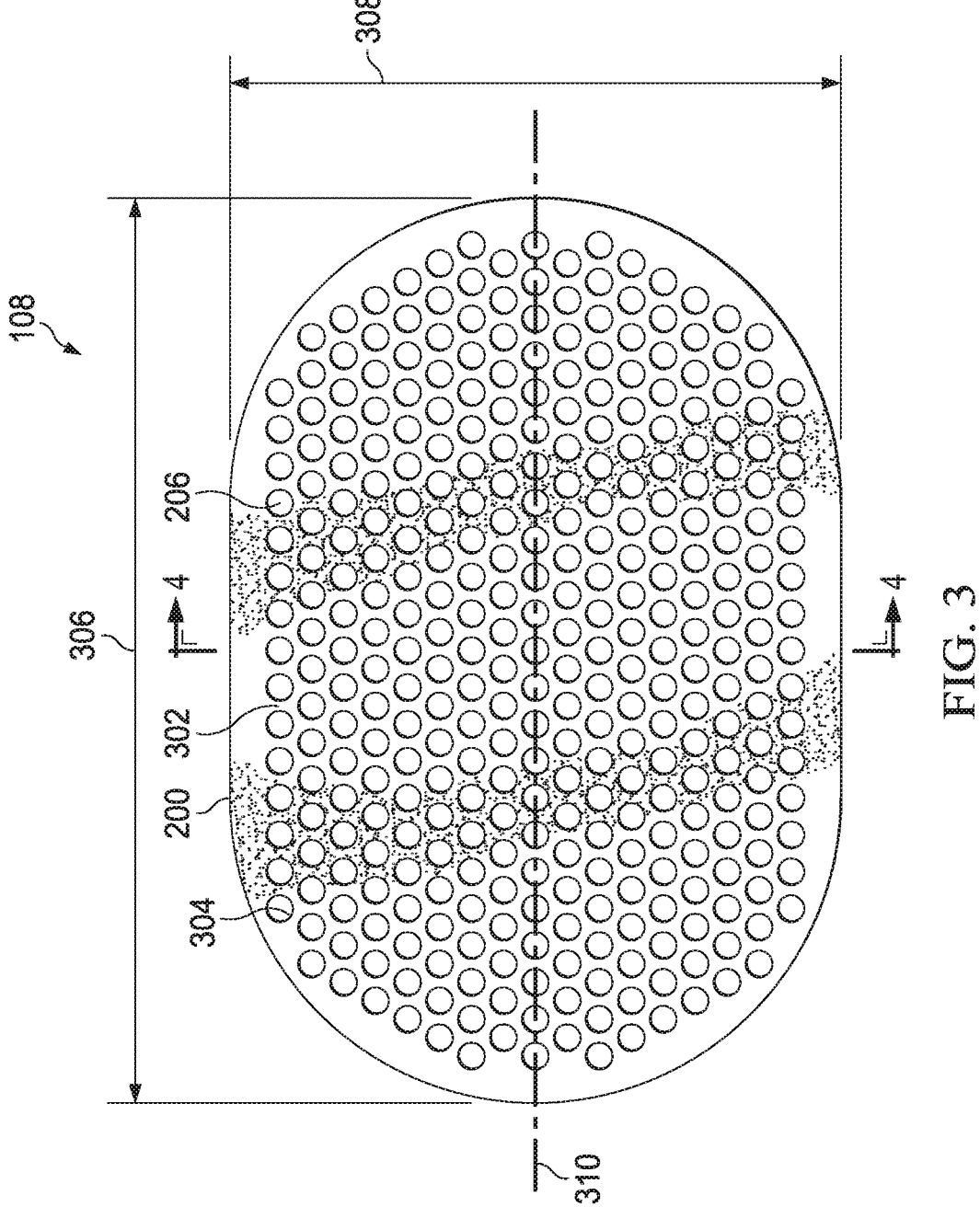
FIG. 3 is a plan view of a tissue interface of FIG. 2, illustrating additional details that may be associated with some embodiments.

FIG. 3 is a plan view of the tissue interface 108 of FIG. 2, illustrating additional details that may be associated with some embodiments. In some embodiments, the plurality of holes 206 may be distributed about the first surface 200 of the tissue interface 108. The plurality of holes 206 can be evenly distributed. In other embodiments, the plurality of holes 206 may be preferentially disposed in a portion of the tissue interface 108.

In some embodiments, the plurality of holes 206 extending into the tissue interface 108 may form walls 302. In some embodiments, an exterior surface of the walls 302 may be parallel to sides of the tissue interface 108. In other embodiments, an interior surface of the walls 302 may be generally perpendicular to the first surface 200 and the second surface 202 of the tissue interface 108. The interior surface or surfaces of the walls 302 may form a perimeter 304 of each hole. In some embodiments, the holes 206 may have a circular shape. In other embodiments, each hole 206 of the plurality of holes 206 may be polygonal, ovular, or amorphous in shape. In some embodiments, the holes 206 may have average effective diameters between about 5 mm and about 20 mm. Preferably, each hole 206 of the plurality of holes 206 may have an average effective diameter of about 10 mm.

In some embodiments, the tissue interface 108 may comprise a length 306 and a width 308. The length 306 of the tissue interface 108 may be between about 180 mm and about 256 mm. The width 308 of the tissue interface 108 may be between about 125 mm and about 150 mm. In some embodiments, the tissue interface 108 may have a contraction axis 310 positioned parallel to the length 306. The contraction axis 310 may also be positioned parallel to the first surface 200 and the second surface 202. In some embodiments, the contraction axis 310 may be used to refer to a desired direction of contraction of the tissue interface 108. For example, the desired direction of contraction of the tissue interface 108 may be perpendicular to the contraction axis 310. In other embodiments, the desired direction of contraction may be parallel to the contraction axis 310. In other embodiments, the desired direction of contraction may be at a non-perpendicular angle to the contraction axis 310. In still other embodiments, the tissue interface 108 may not have a desired direction of contraction.

Figures 4, 5, 6:
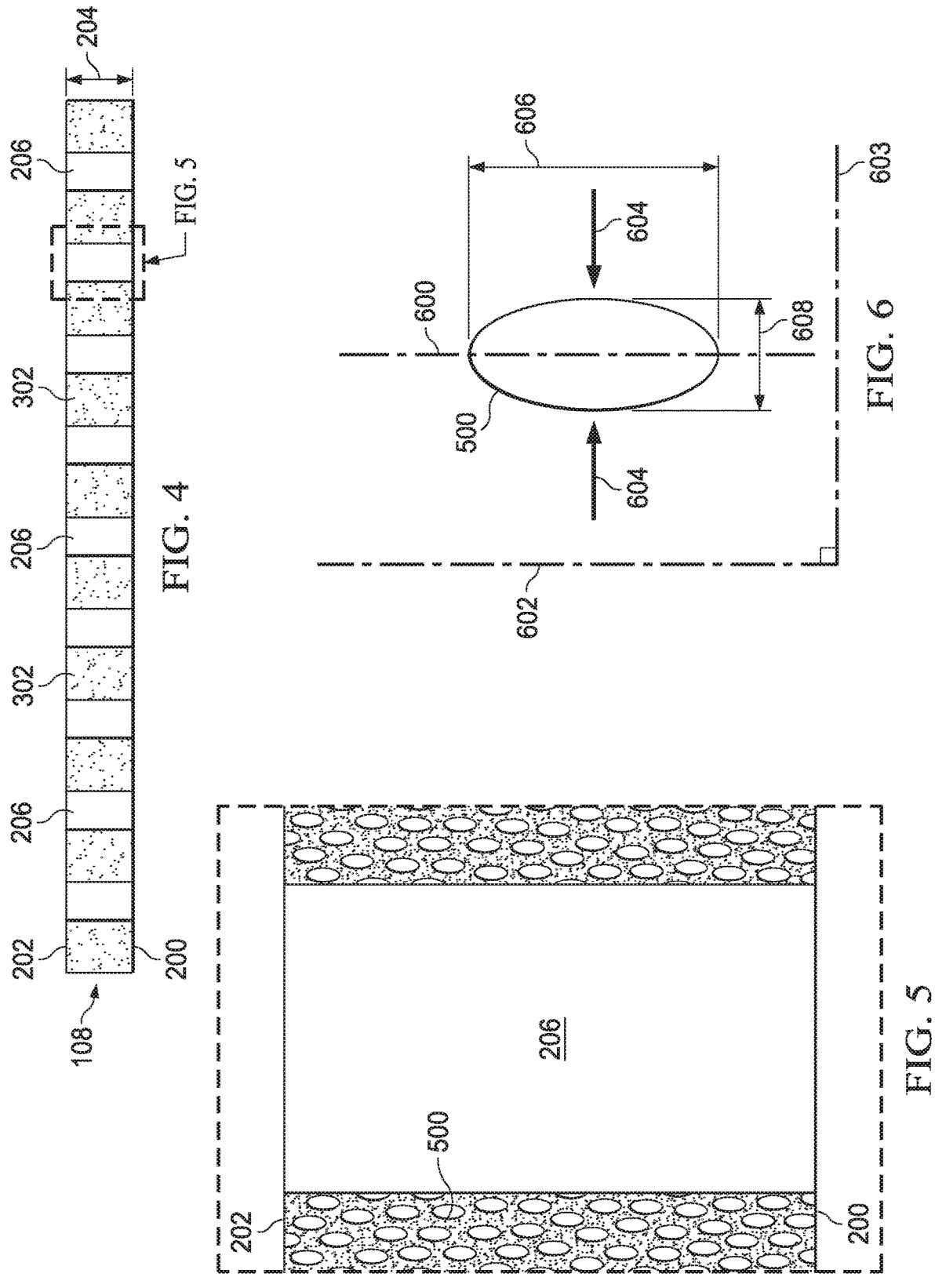
FIG. 4 is a sectional view of the tissue interface of FIG. 3, illustrating additional details that may be associated with some embodiments.
FIG. 5 is a detail view illustrating additional details that may be associated with some embodiments of a plurality of pores of the tissue interface of FIG. 4.
FIG. 6 is a detail view illustrating additional details that may be associated with some embodiments of a pore of FIG. 5.

FIG. 4 is a sectional view taken along line 4-4 of FIG. 3, illustrating additional details that may be associated with some embodiments. In some embodiments, the plurality of holes 206 may extend through the thickness 204 of the tissue interface 108 from the first surface 200 to the second surface 202. The plurality of holes 205 may have a depth that is substantially equal to the thickness 204 of the tissue interface 108. In other embodiments, the plurality of holes 206 may comprise a plurality of blind holes or apertures. For example, the plurality of holes 206 may extend from the first surface 200 toward the second surface 202 at a depth less than the thickness 204 of the tissue interface 108. The depth of the plurality of blind holes or apertures may be between about 5 mm and about 15 mm.

FIG. 5 is a detail view of the tissue interface 108 of FIG. 4, illustrating additional details that may be associated with some embodiments. The tissue interface 108 may be formed from a dressing material such as a foam. For example, cellular foam, open-cell foam, reticulated foam, or porous tissue collections, may be used to form the tissue interface 108. The tissue interface 108 may comprise a plurality of pores 500. In some embodiments, each of the pores 500 of the tissue interface 108 may have pore sizes or average effective diameters in a range of about 60 microns to about 2000 microns. In other embodiments, the pores 500 may have pore sizes or average effective diameters in a range of about 400 microns to about 600 microns. The tensile strength of the tissue interface 108 may vary according to needs of a prescribed therapy. For example, the tensile strength of a foam may be increased for instillation of topical treatment solutions. The 25% compression load deflection of the tissue interface 108 may be at least 0.35 pounds per square inch, and the 65% compression load deflection may be at least 0.43 pounds per square inch. In some embodiments, the tensile strength of the tissue interface 108 may be at least 10 pounds per square inch. The tissue interface 108 may have a tear strength of at least 2.5 pounds per inch. In one non-limiting example, the tissue interface 108 may be an open-cell, reticulated polyurethane foam such as V.A.C.® GRANUFOAM™ Dressing available from Kinetic Concepts, Inc. of San Antonio, Texas; in other embodiments the tissue interface 108 may be an open-cell, reticulated polyurethane foam such as a V.A.C. VERAFLO™ dressing, also available from Kinetic Concepts, Inc., of San Antonio, Texas. In other embodiments, the tissue interface 108 may be formed of an un-reticulated open-cell foam.

In some embodiments, the tissue interface 108 may be formed from a foam that is mechanically or chemically compressed, often as part of a thermoforming process, to increase the density of the foam at ambient pressure. A foam that is mechanically or chemically compressed may be referred to as a compressed foam or a felted foam. A felted foam may be characterized by a firmness factor (FF), which is indicative of the compression of the foam. The firmness factor of a felted foam can be specified as the ratio of original thickness to final thickness. For example, a firmness factor (FF) of 5 may refer to a compressed foam having a density at ambient pressure that is five times greater than a density of the same foam in an uncompressed state at ambient pressure. Generally, a compressed or felted foam may have a firmness factor greater than 1. The degree of compression may affect the physical properties of the felted foam. For example, felted foam has an increased effective density compared to a foam of the same material that is not felted. The felting process can also affect fluid-to-foam interactions. For example, as the density increases, compressibility or collapse may decrease. Therefore, foams which have different compressibility or collapse may have different firmness factors. In some example embodiments, a firmness factor can range from about 2 to about 10 and preferably about 3 to about 5. For example, the firmness factor of the tissue interface 108 felted foam may be about 5 in some embodiments. There is a general linear relationship between firmness level, density, pore size (or pores per inch) and compressibility. For example, foam that is felted to a firmness factor of 3 will show a three-fold density increase and compress to about a third of its original thickness.

In some embodiments, a compressed foam may be a compressed V.A.C.® GRANUFOAM™ Dressing. V.A.C.® GRANUFOAM™ Dressing may have a density of about 0.03 grams per centimeter$^3$ (g/cm3) in its uncompressed state. If the V.A.C.® GRANUFOAM™ Dressing is compressed to have a firmness factor (FF) of 5, the V.A.C.® GRANUFOAM™ Dressing may be compressed until the density of the V.A.C.® GRANUFOAM™ Dressing is about 0.15 g/cm$^3$. V.A.C.® VERAFLO™ dressings may also be compressed to form a compressed foam having a firmness factor (FF) up to 5. For example, V.A.C.® VERAFLO™ Dressing, may have a density between about 1.7 pounds per foot$^3$ (lb/ft$^3$) or 0.027 grams per centimeter$^3$ (g/cm$^3$) and about 2.1 lb/ft$^3$ or 0.034 g/cm$^3$. If the V.A.C.® VERAFLO™ Dressing is compressed to have a firmness factor (FF) of 5, the V.A.C.® VERAFLO™ Dressing may be compressed until the density of the V.A.C.® VERAFLO™ Dressing is between about 0.135 g/cm$^3$ and about 0.17 g/cm$^3$.

Felting comprises a thermoforming process that permanently compresses a foam to increase the density of the foam while maintaining interconnected pathways. For example, felting may be performed by applying heat and pressure to a dressing material that is porous such as a foam material. Some methods may include compressing a foam blank between one or more heated platens or dies (not shown) for a specified period of time and at a specified temperature. In some embodiments, the direction of compression may be parallel to the thickness of the foam block. For example, the direction of the force applied to a blank of the dressing material may be parallel to the thickness and perpendicular to the surface the force is acting on. In other embodiments, the direction of compression may be perpendicular to the thickness of the blank of the dressing material. For example, the direction of the force applied to a foam blank of the dressing material may act on the thickness and be parallel to a surface perpendicular to the thickness.

The period of time of compression may range from 10 minutes up to 24 hours, though the time period may be more or less depending on the specific type of dressing material used. Further, in some examples, the temperature may range between 120° C. to 260° C. Generally, the lower the temperature of the platen, the longer a dressing material must be held in compression. After the specified time period has elapsed, the pressure and heat will form a felted structure or surface on or through the dressing material or a portion of the dressing material.

Generally, if a compressed foam is subjected to negative pressure, the compressed foam exhibits less deformation than a similar uncompressed foam. If the tissue interface 108 is formed of a compressed foam, the thickness 204 of the tissue interface 108 may deform less than if the tissue interface 108 is formed of a comparable uncompressed foam. The decrease in deformation may be caused by the increased stiffness as reflected by the firmness factor (FF). If subjected to the stress of negative pressure, the tissue interface 108 that is formed of compressed foam may flatten less than the tissue interface 108 that is formed from uncompressed foam. Consequently, if negative pressure is applied to the tissue interface 108, the stiffness of the tissue interface 108 in the direction parallel to the thickness 204 of the tissue interface 108 allows the tissue interface 108 to be more compliant or compressible in other directions, e.g., a direction perpendicular to the thickness 204. The foam material used to form a compressed foam may be either hydrophobic or hydrophilic. The foam material used to form a compressed foam may also be either reticulated or un-reticulated.

The density of the foam is generally increased by felting. In some embodiments, contact with hot-press platens in the felting process can also result in a density gradient in which the density is greater at the surface and the pore size is smaller at the surface. In some embodiments, the felted structure may be comparatively smoother than any unfinished or non-felted surface or portion of the dressing material. Further, the pores 500 in the felted structure may be smaller than the pores throughout any unfinished or non-felted surface or portion of the dressing material. In some examples, the felted structure may be applied to all surfaces or portions of the dressing material. Further, in some examples, the felted structure may extend into or through an entire thickness of the dressing material such that the all of the dressing material is felted.

The pore size of a foam material may vary according to needs of the tissue interface 108 and the amount of compression of the foam. For example, in some embodiments, the pores of an uncompressed foam may have pore sizes in a range of about 400 microns to about 600 microns. If the same foam is compressed, the pores of the compressed foam may have pore sizes that are smaller than when the foam is in its uncompressed state.

The felting process may alter certain properties of the original material, including pore shape and/or size, elasticity, density, and density distribution. For example, struts that define the plurality of pores 500 in the foam may be deformed during the felting process. The deformed struts can decrease the elasticity of the foam. The deformed struts can also cause a flattening in pore shapes. For example, an un-felted foam may have a plurality of pores having a substantially circular or spherical shape. By felting the foam, the pores 500 of the tissue interface 108 may have a non-circular shape. In some embodiments, each of the plurality of pores 500 may have a generally elliptical or ovoid shape.

The deformation of the struts and pore shape can be applied preferentially. For example, the pores 500 can be deformed so that a shape of each of the pores 500 is oriented in a particular direction within the tissue interface 108. In some embodiments, the orientation of the pores 500 can be controlled by felting the dressing material. For example, the pores 500 can be deformed so that the deformation of the pores 500 is oriented with respect to a surface of the tissue interface 108 that is intended to contact the tissue site. In some embodiments, the pores 500 can be preferentially deformed with respect to the first surface 200. For example, a blank of the dressing material forming the tissue interface 108 can be felted by applying heat and compression to the thickness 204. The direction of the force applied to the dressing material is parallel to the first surface 200 of the tissue interface 108.

FIG. 6 is a detail view illustrating additional details that may be associated with some embodiments of the plurality of pores 500 of FIG. 5. In FIG. 6, a single pore of the plurality of pores 500 of the tissue interface 108 is shown. In some embodiments, the tissue interface 108 may have a first axis 602 and a second axis 603. The first axis 602 may be parallel to the thickness 204 and perpendicular to the first surface 200 and the second surface 202 of the tissue interface 108. The second axis 603 may be perpendicular to the first axis 602 and parallel to the first surface 200 and the second surface 202 of the tissue interface 108.

In some embodiments, each of the plurality of pores 500 may be oriented at an angle to the first surface 200 and the second surface 202 of the tissue interface 108. For example, each pore 500 of the plurality of pores 500 may have a major axis 600 extending through a center of the pore 500. The major axis 600 may be oriented parallel to the first axis 602 and perpendicular to the second axis 603. In some embodiments, the major axis 600 may be oriented perpendicular to the first surface 200 and the second surface 202 and parallel to the thickness 204. In some embodiments, the major axis 600 may be oriented at an angle to the second axis 603. For example, the angle between the second axis 603 and the major axis 600 may be about 90°. In some embodiments, each pore 500 of the plurality of pores 500 may have a pore length 606 extending generally parallel to the major axis 600 and a pore width 608 extending generally perpendicular to the major axis 600. In some embodiments, the pore length 606 of the plurality of pores 500 may be greater than the pore width 608.

The pores 500 may be oriented by the manufacturing process. During felting, a force 604 can be applied to a foam blank of the dressing material. The force 604 can change the shape of the pore 500 by forcing surfaces of the pore 500 perpendicular to the force 604 toward each other and pushing surfaces parallel to the force 604 away from each other. As a result, the pore 500 stretches parallel to the first axis 602 and compresses parallel to the second axis 603. The heat applied during the felting process can set the pore 500 in the shape formed by the force 604. In other embodiments, the force 604 can be applied at a non-normal angle to the first axis 602, causing the pore 500 to compress at an angle to the first axis 602 and stretch at an angle to the first axis 602. Generally, the pore width 608 of the pore 500 may be parallel to the direction of the force 604 and the pore length 606 of the pore 500 may be perpendicular to the direction of the force 604.

In some embodiments, the orientation of the plurality of pores 500 may allow the plurality of pores 500 to compress more in a direction parallel to the second axis 603 and resist compression in a direction parallel to the first axis 602. For example, each of the plurality of pores 500 may be configured to contract in a direction perpendicular to the major axis 600. In some embodiments, each of the plurality of pores 500 may be configured to contract in a direction parallel to the first surface 200 and the second surface 202. In some embodiments, each of the plurality of pores 500 may be configured to contract in all directions toward the major axis 600. In some embodiments, the pores 500 may resist collapse more in a direction parallel to the major axis 600 than in a direction perpendicular to the major axis 600. As a result, the tissue interface 108 formed form the pores 500 may collapse laterally under negative pressure. See, for example, the following experimental data.

The following samples were provided: three unfelted Granufoam blocks with a starting size of 25 mm (height) by 25 mm (width) and approximately spherical pores, three 3× felted (e.g., firmness factor of 3) Granufoam blocks with starting size of 25 mm (height) by 25 mm (width) and ovoid pores oriented with the major axis approximately parallel to the thickness (e.g., height), and three 5× felted (e.g., firmness factor of 5) Granufoam blocks with starting size of 25 mm (height) by 25 mm (width) and ovoid pores oriented with the major axis approximately parallel to the thickness (e.g., height). Negative pressure of approximately −125 mmHg was applied to all three samples, and the height and width measurements under applied negative pressure were recorded as follows:

| Material | Sample 1 | | Sample 2 | | Sample 3 | | Average | |
|---|---|---|---|---|---|---|---|---|
| | Height (mm) | Width (mm) | Height (mm) | Width (mm) | Height (mm) | Width (mm) | Height (mm) | Width (mm) |
| Unfelted Granufoam | 4.53 | 24.56 | 3.98 | 24.83 | 4.47 | 24.33 | 4.33 | 24.57 |
| 3X Felted with major axis parallel to thickness | 14.25 | 15.84 | 14.11 | 14.03 | 15.62 | 13.80 | 14.66 | 14.56 |
| 5X Felted with major axis parallel to thickness | 20.08 | 18.03 | 21.13 | 17.81 | 20.56 | 17.69 | 20.59 | 17.84 |

In some embodiments, the felted foam with ovoid pores oriented with the major axis approximately parallel to the thickness (e.g., height) may draw down in thickness under applied negative pressure approximately ½ or less the amount compared to similar unfelted foam. For example, the felted foam with ovoid pores oriented with the major axis approximately parallel to the thickness may draw down in thickness under applied negative pressure approximately ½-⅕ the amount compared to similar unfelted foam. In some embodiments, the felted foam with ovoid pores oriented with the major axis approximately parallel to the thickness may have lateral contraction under applied negative pressure of approximately 16 or more times greater than the amount compared to similar unfelted foam. For example, the felted foam with ovoid pores oriented with the major axis approximately parallel to the thickness may have lateral contraction under applied negative pressure which is approximately 16-24 times greater than the amount compared to similar unfelted foam.

In some embodiments, resistance to contraction in thickness due to orientation of the ovoid pores may maintain a surface area that will transmit a higher lateral force under applied negative pressure as compared to the lateral force from similar unfelted foam. For example, 3× felted foam (e.g. foam with a firmness factor of 3) with ovoid pores oriented approximately parallel to the thickness may have a lateral force which is approximately 30-70% better than similar unfelted foam, under applied negative pressure. Similarly, if a specific lateral force is desired under applied negative pressure, then that amount of lateral force may be generated using less negative pressure when felted foam with ovoid pores oriented approximately parallel to the thickness is used instead of similar unfelted foam.

Figure 7:
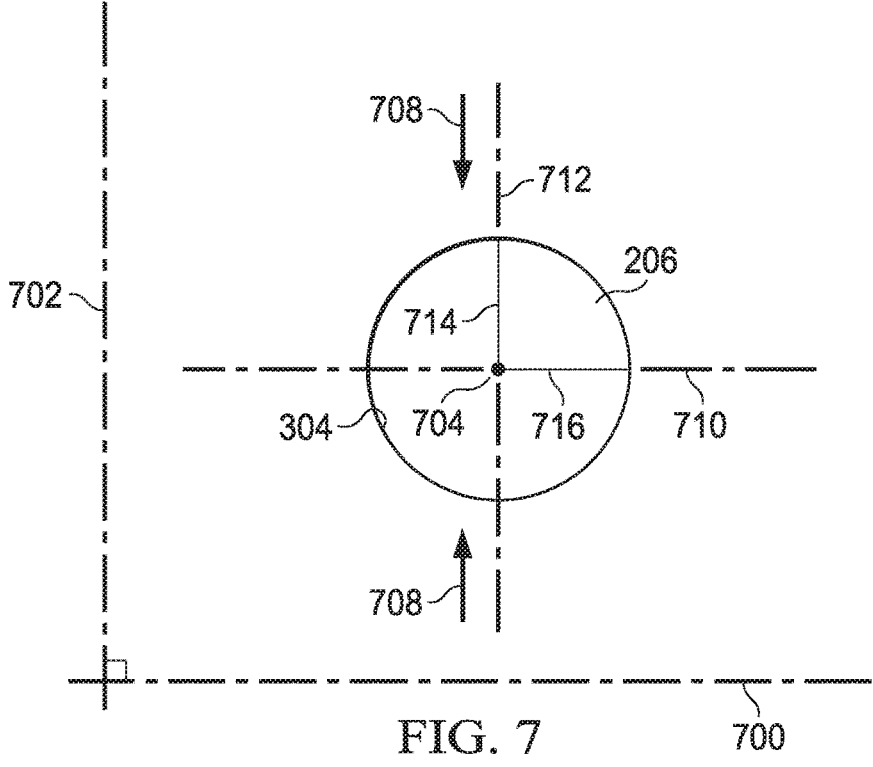
FIG. 7 is a plan view illustrating additional details that may be associated with some embodiments of a hole of the tissue interface of FIG. 3.

FIG. 7 is a plan view illustrating additional details that may be associated with some embodiments of a hole 206 of the tissue interface 108 of FIG. 3. In FIG. 7, a single hole 206 having a circular shape is shown. The hole 206 may include a center 704 and the perimeter 706. The hole 206 may have a perforation shape factor (PSF). The perforation shape factor (PSF) may represent an orientation of the hole 206 relative to a first orientation line 700 and a second orientation line 702. Generally, the perforation shape factor (PSF) is a ratio of ½ a maximum length of the hole 206 that is parallel to the desired direction of contraction to ½ a maximum length of the hole 206 that is perpendicular to the desired direction of contraction. For descriptive purposes, the desired direction of contraction is parallel to the second orientation line 702. The desired direction of contraction may be indicated by a lateral force 708. For reference, the hole 206 may have an X-axis 710 extending through the center 704 parallel to the first orientation line 700, and a Y-axis 712 extending through the center 704 parallel to the second orientation line 702. The perforation shape factor (PSF) of the hole 206 may be defined as a ratio of a line segment 714 on the Y-axis 712 extending from the center 704 to the perimeter 706 of the hole 206, to a line segment 716 on the X-axis 710 extending from the center 704 to the perimeter 706 of the hole 206. If a length of the line segment 714 is 2.5 mm and the length of the line segment 716 is 2.5 mm, the perforation shape factor (PSF) would be 1. In other embodiments, the holes 206 may have other shapes and orientations, for example, oval, hexagonal, square, triangular, or amorphous or irregular and be oriented relative to the first orientation line 700 and the second orientation line 702 so that the perforation shape factor (PSF) may range from about 0.5 to about 1.10.

Figure 8:
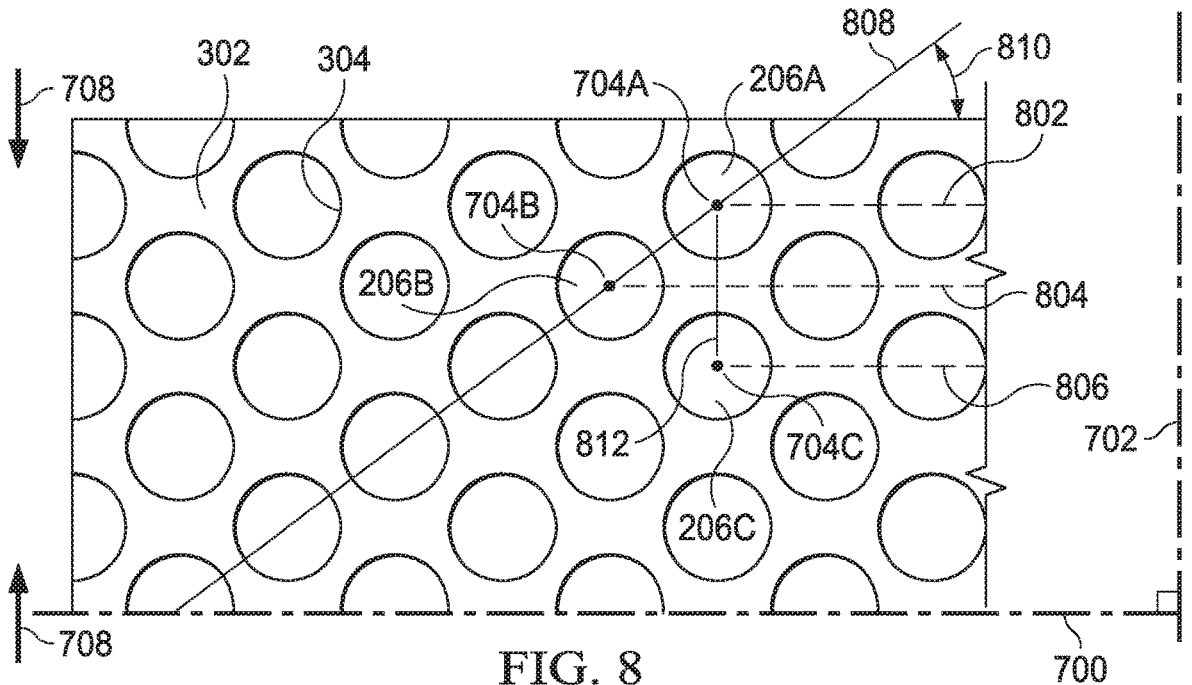
FIG. 8 is a plan view illustrating additional details of a portion of the tissue interface of FIG. 3.

FIG. 8 is a plan view illustrating additional details of the plurality of holes 206 of the tissue interface 108 of FIG. 3. As illustrated in FIG. 8, the tissue interface 108 may include the plurality of holes 206 aligned in parallel rows to form an array. The array of holes 206 may include a first row 802 of the holes 206, a second row 804 of the holes 206, and a third row 806 of the holes 206. In some embodiments, a width of the wall 302 between the perimeters 304 of adjacent holes 206 in a row, such as the first row 802, may be between about 13 mm about 15 mm. In some embodiments, the width of the wall 302 between perimeters 304 of adjacent holes may preferably be 14 mm.

In some embodiments, a line connecting the centers of adjacent rows may form a strut angle (SA) with the first orientation line 700. For example, a first hole 206A in the first row 802 may have a center 704A, and a second hole 206B in the second row 804 may have a center 704B. A strut line 808 may connect the center 704A with the center 704B.

The strut line 808 may form an angle 810 with the first orientation line 700. The angle 810 may be the strut angle (SA) of the tissue interface 108. In some embodiments, the strut angle (SA) may be less than about 90°. In other embodiments, the strut angle (SA) may be between about 30° and about 70° relative to the first orientation line 700. In other embodiments, the strut angle (SA) may be about 66° from the first orientation line 700. Generally, as the strut angle (SA) decreases, a stiffness of the tissue interface 108 in a direction parallel to the first orientation line 700 may increase. Increasing the stiffness of the tissue interface 108 parallel to the first orientation line 700 may increase the compressibility of the tissue interface 108 perpendicular to the first orientation line 700. Consequently, if negative pressure is applied to the tissue interface 108, the tissue interface 108 may be more compliant or compressible in a direction perpendicular to the first orientation line 700. By increasing the compressibility of the tissue interface 108 in a direction perpendicular to the first orientation line 700, the tissue interface 108 may collapse to apply the lateral force 708 to the tissue site as described in more detail below.

In some embodiments, the centers 704 of the holes 206 in alternating rows, for example, the center 704A of the first hole 206A in the first row 802 and a center 704C of a hole 206C in the third row 806, may be spaced from each other parallel to the second orientation line 702 by a length 812. In some embodiments, the length 812 may be greater than an effective diameter of the hole 206. If the centers 704 of holes 206 in alternating rows are separated by the length 812, the exterior surface of the walls 302 parallel to the first orientation line 700 may be considered continuous. Generally, the exterior surface of the walls 302 may be continuous if the exterior surface of the walls 302 do not have any discontinuities or breaks between holes 206. In some embodiments, the length 812 may be between about 4 mm and about 6 mm.

In some embodiments, the holes 206 may be formed during molding of the tissue interface 108. In other embodiments, the holes 206 may be formed by cutting, melting, drilling, or vaporizing the tissue interface 108 after the tissue interface 108 is formed. For example, the holes 206 may be formed in the tissue interface 108 by laser cutting the compressed foam of the tissue interface 108. In some embodiments, the holes 206 may be formed so that the interior surfaces of the walls 302 of the holes 206 are parallel to the thickness 204. In other embodiments, the holes 206 may be formed so that the interior surfaces of the walls 302 of the holes 206 form a non-perpendicular angle with the first surface 200. In still other embodiments, the interior surfaces of the walls 302 of the holes 206 may taper toward the center 704 of the holes 206 to form conical, pyramidal, or other irregular through-hole shapes. If the interior surfaces of the walls 302 of the holes 206 taper, the holes 206 may have a height less than the thickness 204 of the tissue interface 108.

Figure 9:
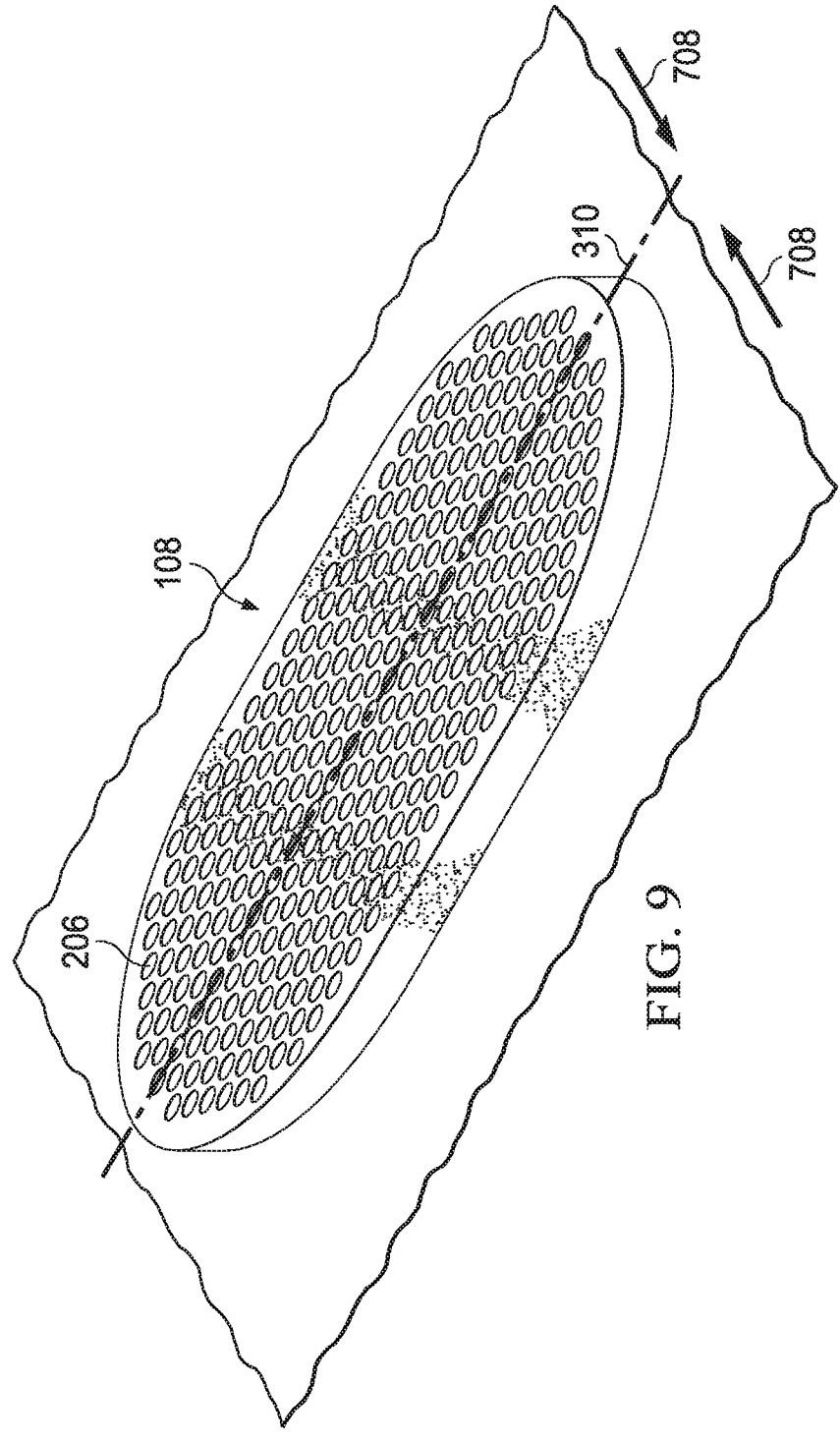
FIG. 9 is a plan view illustrating additional details of the tissue interface of FIG. 3 in a contracted state.

FIG. 9 is a plan view illustrating additional details of the tissue interface 108 of FIG. 3 in a contracted state. If the tissue interface 108 is positioned on the tissue site, the tissue interface 108 may generate the lateral force 708 perpendicular to the contraction axis 310, contracting the tissue interface 108 as shown. In operation, negative pressure is supplied to the sealed space with the negative-pressure source 102. In response to the supply of negative pressure, the tissue interface 108 contracts from the relaxed position illustrated in FIG. 3 to the contracted positioned illustrated in FIG. 9. When the negative pressure is removed, for example, by venting the negative pressure from the sealed space, the tissue interface 108 expands back to the relaxed position. If the tissue interface 108 is cycled between the contracted and relaxed positioned of FIG. 3 and FIG. 9, respectively, the first surface 200 of the tissue interface 108 may disrupt debris on the tissue site by rubbing the debris from the tissue site. The edges of the holes 206 formed by the first surface 200 and the interior surfaces or transverse surfaces of the walls 302 can form cutting edges that can disrupt the debris in the tissue site, allowing the debris to exit though the holes 206. In some embodiments, the cutting edges are defined by the perimeter 304 where each hole 206 intersects the first surface 200.

Figure 10:
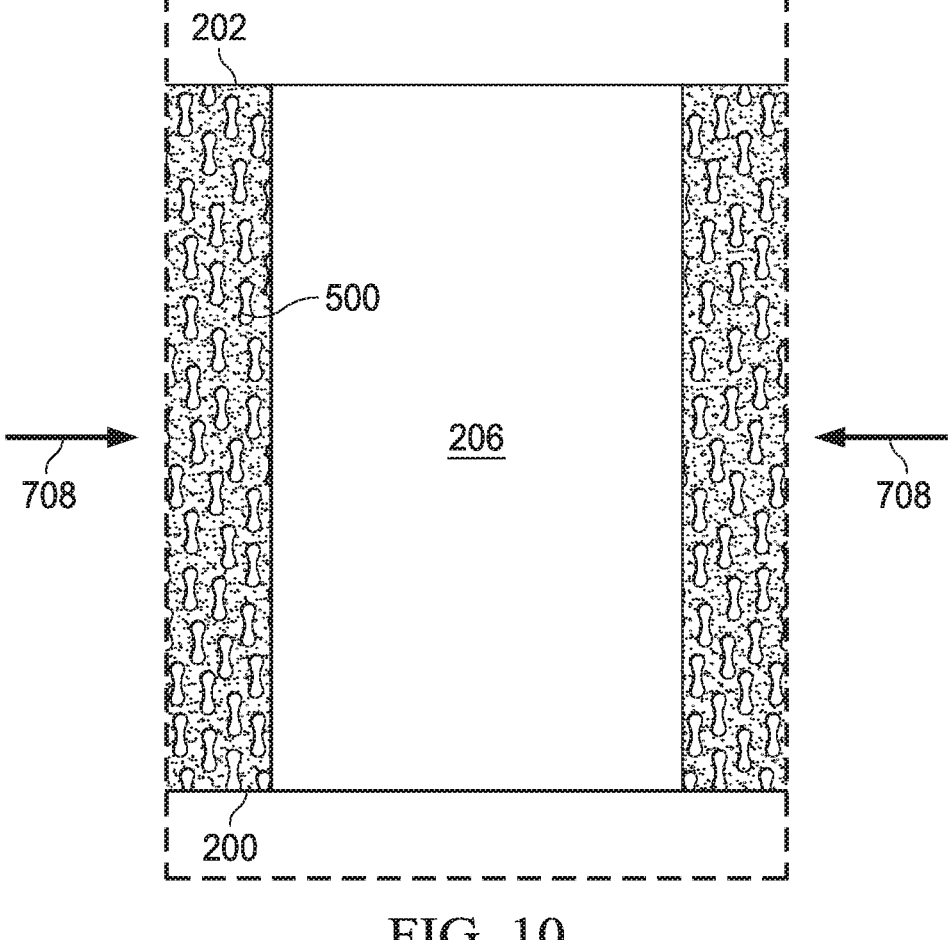
FIG. 10 is a detail view illustrating additional details that may be associated with the plurality of pores of the tissue interface of FIG. 5 in a contracted state.

FIG. 10 is a detail view illustrating additional details that may be associated with the plurality of pores 500 of the tissue interface 108 of FIG. 5 in a contracted state or a contracted position. In response to the supply of negative pressure, the plurality of pores 500 may collapse from the relaxed positioned illustrated in FIG. 5 to the contracted position illustrated in FIG. 10. For example, the plurality of pores 500 may be configured to collapse in a direction parallel to the first surface 200 and the second surface 202 of the tissue interface 108, as indicated by the lateral force 708. The ovular shape of the plurality of pores 500 combined with the plurality of holes 206 allows the tissue interface 108 to contract laterally, as indicated by the lateral force 708, debriding tissue. In some embodiments, the lateral force 708 may be perpendicular to the contraction axis 310. In still other embodiments, the lateral force 708 may be generated at an angle to the contraction axis 310.

Figure 11:
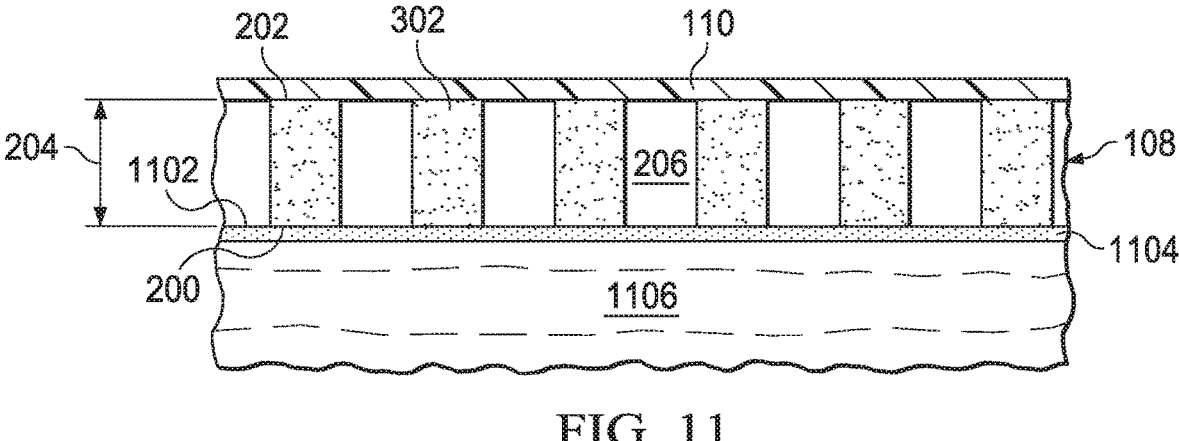
FIG. 11 is a sectional view of a portion of the tissue interface of FIG. 2, illustrating additional details that may be associated with some embodiments.

FIG. 11 is a sectional view of a portion of the dressing 104 of FIG. 2, illustrating additional details that may be associated with some embodiments. The tissue interface 108 may be placed at a tissue site 1102 having debris 1104 covering subcutaneous tissue 1106. For example, a clinician may place the tissue interface 108 at the tissue site 1102. In some embodiments, the length 306 and the width 308 of the tissue interface 108 may be greater than an opening of the tissue site 1102. The tissue interface 108 may be sized to permit the tissue interface 108 to be passed through the opening of the tissue site 1102 to be placed adjacent to the debris 1104. Sizing can include removing a portion of the tissue interface 108 for example, by cutting, tearing, melting, dissolving, vaporizing, or otherwise separating a portion of the tissue interface 108 from remaining portions of the tissue interface 108. Following sizing and placement of the tissue interface 108 at the tissue site 1102, the cover 110 may be placed over the tissue interface 108 to provide a sealed environment for the application of negative-pressure therapy or instillation therapy.

Figure 12:
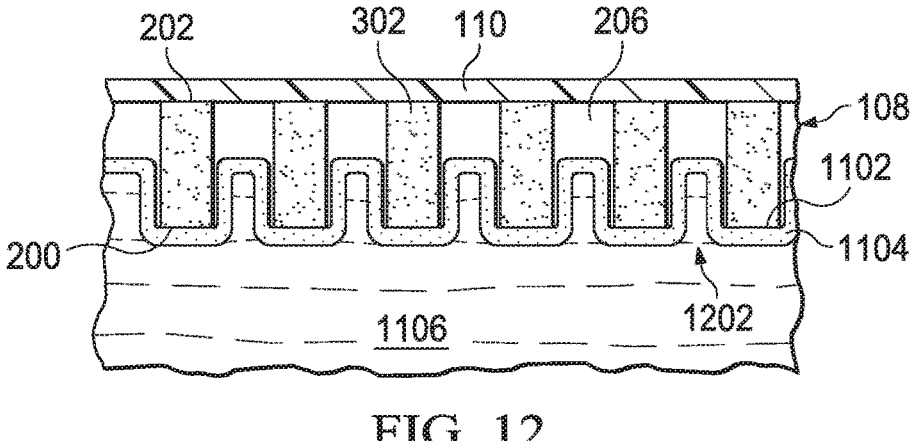
FIG. 12 is a sectional view of the tissue interface of FIG. 2 during negative-pressure therapy, illustrating additional details that may be associated with some embodiments.

FIG. 12 is a sectional view of a portion of the dressing 104 of FIG. 2 during negative-pressure therapy, illustrating additional details that may be associated with some embodiments. For example, FIG. 12 may illustrate a moment in time where a pressure in the sealed environment may be about −125 mm Hg of negative pressure. In response to the application of negative pressure, the pores 500 of the tissue interface 108 oriented so that the pore length 606 of the pores 500 is parallel to the thickness 204 and the pore width 608 of the pores 500 is parallel to the first surface 200 may resist collapse. In response, the tissue interface 108 may not compress or may compress minimally. Preferably, the thickness 204 remains substantially the same. In other embodiments, the thickness 204 of the tissue interface 108 during negative-pressure therapy may be slightly less than the thickness 204 of the tissue interface 108 if the pressure in the sealed environment is about the ambient pressure.

In some embodiments, negative pressure in the sealed environment can generate concentrated stresses in the tissue interface 108 and the debris 1104 adjacent to the holes 206 in the tissue interface 108. The concentrated stresses can cause macro-deformations of the debris 1104 and the subcutaneous tissue 1106 that draws portions of the debris 1104 and the subcutaneous tissue 1106 into the holes 206. For example, as the holes 206 collapse in the direction parallel to the first surface 200 and the second surface 202 under negative pressure, portions of the subcutaneous tissue 1106 and the debris 1104 may be drawn into the holes 206 by a pinching action. Additionally, as the tissue interface 108 resists compression in the direction parallel to the thickness 204, portions of the subcutaneous tissue 1106 and the debris 1104 may be drawn into the thickness 204 of the tissue interface 108 under negative pressure.

In some embodiments, the holes 206 of the tissue interface may create macro-pressure points in portions of the debris 1104, and the subcutaneous tissue 1106 that are in contact with the first surface 200 of the tissue interface 108, causing tissue puckering and nodules 1202 in the debris 1104 and the subcutaneous tissue 1106. A height of the nodules 1202 over the surrounding tissue may be selected to maximize disruption of debris 1104 and minimize damage to subcutaneous tissue 1106 or other desired tissue. Generally, the pressure in the sealed environment can exert a force that is proportional to the area over which the pressure is applied. At the holes 206 of the tissue interface 108, the force may be concentrated as the resistance to the application of the pressure is less than in the walls 302 of the tissue interface 108. In response to the force generated by the pressure at the holes 206, the debris and the subcutaneous tissue 1106 that forms the nodules 1202 may be drawn into the holes 206 until the force applied by the pressure is equalized by the reactive force of the debris 1104, and the subcutaneous tissue 1106. In some embodiments where the negative pressure in the sealed environment may cause tearing, the depth of the holes 206 may be selected to limit the height of the nodules 1202 over the surrounding tissue. In some embodiments, the height of the nodules 1202 may be limited to a height that is less than the depth of the holes 206. In an exemplary embodiment, the depth of the holes 206 may be about 8 mm. During the application of negative pressure, the height of the nodules 1202 may be limited to about 2 mm to about 8 mm. By controlling the height of the nodules 1202 by controlling the depth of the holes 206, the aggressiveness of disruption to the debris 1104 and tearing can be controlled.

In some embodiments, the formation of the nodules 1202 can cause the debris 1104 to remain in contact with the tissue interface 108 during negative pressure therapy. For example, the nodules 1202 may contact the sidewalls of the holes 206 of the tissue interface 108. In some embodiments, formation of the nodules 1202 may lift debris 1104 and particulates off the surrounding tissue, operating in a piston-like manner to move debris 1104 toward the cover 110 and out of the sealed environment.

In response to the return of the sealed environment to ambient pressure, the nodules 1202 may leave the holes 206, returning to the position shown in FIG. 11. In some embodiments, repeated application of negative-pressure therapy and instillation therapy while the tissue interface 108 is disposed over the debris 1104 may disrupt the debris 1104, allowing the debris 1104 to be removed during dressing changes. In other embodiments, the tissue interface 108 may disrupt the debris 1104 so that the debris 1104 can be removed by negative pressure. In still other embodiments, the tissue interface 108 may disrupt the debris 1104, aiding removal of the debris 1104 during debridement processes. With each cycle of therapy, the tissue interface 108 may form nodules 1202 in the debris 1104. The formation of the nodules 1202 and release of the nodules 1202 by the tissue interface 108 during therapy may disrupt the debris. With each subsequent cycle of therapy, disruption of the debris 1104 can be increased.

Disruption of the debris 1104 can be caused, at least in part, by the concentrated forces applied to the debris 1104 by the holes 206 and the walls 302 of the tissue interface 108. The forces applied to the debris 1104 can be a function of the negative pressure supplied to the sealed environment and the area of each hole 206. For example, if the negative pressure supplied to the sealed environment is about −125 mm Hg and the diameter of each hole 206 is about 5 mm, the force applied at each hole 206 is about 0.07 lbs. If the diameter of each hole 206 is increased to about 8 mm, the force applied at each hole 206 can increase up to 6 times. Generally, the relationship between the diameter of each hole 206 and the applied force at each hole 206 is not linear and can increase exponentially with an increase in diameter.

In some embodiments, the negative pressure applied by the negative-pressure source 102 may be cycled rapidly. For example, negative pressure may be supplied for a few seconds, then vented for a few seconds, causing a pulsation of negative pressure in the sealed environment. The pulsation of the negative pressure can pulsate the nodules 1202, causing further disruption of the debris 1104.

In some embodiments, the cyclical application of instillation therapy and negative pressure therapy may cause micro-floating. For example, negative pressure may be applied to the sealed environment during a negative-pressure therapy cycle. Following the conclusion of the negative-pressure therapy cycle, instillation fluid may be supplied during the instillation therapy cycle. The instillation fluid may cause the tissue interface 108 to float relative to the debris. As the tissue interface 108 floats, it may change position relative to the position the tissue interface 108 occupied during the negative-pressure therapy cycle. The position change may cause the tissue interface 108 to engage a slightly different portion of the debris 1104 during the next negative-pressure therapy cycle, aiding disruption of the debris 1104.

A method of manufacturing a dressing for a tissue site is also described herein, wherein some example embodiments include providing a dressing material having a surface configured to contact the tissue site. The dressing material may have a plurality of pores. In some embodiments, the dressing material may comprise an open-cell reticulated foam. The method may further comprise applying a compressive force to the dressing material at an angle to the surface, causing a permanent deformation of the plurality of pores. In some embodiments, the angle may be about 90°. In some embodiments, applying the compressive force to the dressing material may comprise increasing a density of the dressing material. In some embodiments, the method may further comprise forming a plurality of holes in the dressing material. The plurality of holes may extend into the dressing material from the surface. In some embodiments, the plurality of holes may be formed in the dressing material after applying the compressive force to the dressing material. In some embodiments, the method may further comprise heating the dressing material.

In some embodiments, causing the permanent deformation of the plurality of pores may comprise forming a plurality of compressed pores. Forming a plurality of compressed pores may comprise compressing the pores from a generally circular shape to a generally ovular shape. In some embodiments, the method may further comprise orienting a major axis of the ovular-shaped pores perpendicular to the surface. In some embodiments, the plurality of compressed pores may be configured to collapse from a relaxed position to a contracted position in response to an application of negative pressure. In some embodiments, the plurality of compressed pores may be configured to collapse in a direction parallel to the surface.

Alternatively, other example embodiments may describe a system for providing negative-pressure therapy to a tissue site. The system can include a tissue interface, a sealing member configured to be disposed over the tissue interface to create a sealed space, and a negative pressure source fluidly coupled to the sealed space. In some embodiments, the sealing member may comprise a polymer film. In some embodiments, the sealing member may be configured to be coupled to the second surface of the tissue interface with an adhesive. The tissue interface can include a first surface configured to face the tissue site; a second surface opposite the first surface; a thickness extending from the first surface to the second surface; and a plurality of pores, each of the pores having an ovoid shape oriented at an angle to the first surface. In some embodiments, the angle may be about 90°. In some embodiments, the plurality of pores may be configured to contract in a direction parallel to the first surface and the second surface.

A tissue interface for treating a tissue site, is also described herein, wherein the tissue interface can be formed by a process including providing a dressing material and applying a compressive force to the dressing material. The dressing material can have a surface configured to contact the tissue site and a plurality of pores. The compressive force can be applied to the dressing material at an angle to the surface. The compressive force can also cause permanent deformation of the plurality of pores. In some embodiments, applying a compressive force to the dressing material may include compressing the dressing material from a first thickness to a second thickness. In some embodiments, the first thickness may be greater than the second thickness.

A method of treating a tissue site is also described herein. Some example embodiments include applying a tissue interface to the tissue site. The tissue interface may comprise a first surface configured to face the tissue site, a second surface opposite the first surface, a thickness extending from the first surface to the second surface, and a plurality of pores having an elliptical shape and a major axis oriented perpendicular to the first surface and the second surface. In some embodiments, the plurality of pores are configured to contract in a direction parallel to the first surface and the second surface. The method further comprises covering the tissue interface with a cover to form a sealed space continuing the tissue interface, fluidly coupling a fluid conductor to the tissue interface, fluidly coupling a negative-pressure source to the fluid conductor, applying negative pressure from the negative pressure source to the tissue interface through the fluid conductor, and contracting the tissue interface from a first width to a second width in response to an application of negative pressure to the tissue interface. The second width may be less than the first width.

The systems, apparatuses, and methods described herein may provide significant advantages. For example, the embodiments described herein provide a tissue interface that can contract in a lateral direction, while resisting vertical compression. The lateral contraction and resistance to vertical compression can provide improved wound healing and cleansing. For example, the tissue interface can contract in a direction parallel to the surface of the tissue site, loosening slough and providing tissue debridement.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 112 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site, the dressing comprising a tissue interface having:
   a first surface configured to face the tissue site;
   a second surface opposite the first surface;
   a thickness extending from the first surface to the second surface;
   a plurality of pores, the plurality of pores having an elliptical shape and a major axis of the plurality of pores being oriented perpendicular to the first surface and the second surface; and
   a plurality of holes disposed in the first surface and extending from the first surface toward the second surface to form walls perpendicular to the first surface, a minor axis of the plurality of pores being oriented perpendicular to a surface of the walls of the plurality of holes.

2. The dressing of claim 1, wherein the plurality of pores are configured to contract in a direction parallel to the first surface and the second surface.

3. The dressing of claim 1, further comprising a dressing length and a dressing width.

4. The dressing of claim 3, wherein the major axis is positioned perpendicular to the dressing length and parallel to the thickness.

5. The dressing of claim 1, wherein the plurality of pores are configured to contract in a direction perpendicular to the major axis.

6. The dressing of claim 1, further comprising a cover layer configured to be disposed over the second surface of the tissue interface.

7. The dressing of claim 6, wherein the cover layer comprises a liquid-impermeable film.

8. The dressing of claim 6, wherein the cover layer comprises a polymer film.

9. The dressing of claim 6, further comprising a fluid port configured to be coupled to the cover layer and fluidly coupled to the tissue interface.

10. The dressing of claim 1, wherein the tissue interface comprises a felted foam.

11. The dressing of claim 10, wherein the felted foam is felted to a firmness factor of 2 to 10.

12. The dressing of claim 10, wherein the felted foam has an uncompressed density of about 0.027 to about 0.034 g/cm³.

13. The dressing of claim 1, wherein the thickness of the tissue interface is between about 5 mm to about 15 mm.

14. The dressing of claim 1, wherein the plurality of holes are blind holes.

15. The dressing of claim 14, wherein the plurality of holes have a depth between about 5 mm to about 15 mm.

16. The dressing of claim 1, wherein the plurality of holes extend through the thickness of the tissue interface from the first surface to the second surface.

17. A system for providing negative-pressure therapy to a tissue site, the system comprising:

a tissue interface comprising:

a first surface configured to face the tissue site, a second surface opposite the first surface, a thickness extending from the first surface to the second surface, a plurality of pores, each pore of the plurality of pores having an ovoid shape oriented at an angle to the first surface, and a plurality of apertures extending from the first surface toward the second surface to form walls perpendicular to the first surface, a minor axis of the plurality of pores being oriented perpendicular to a surface of the walls of the plurality of apertures;

a sealing member configured to be disposed over the tissue interface to create a sealed space; and a negative pressure source fluidly coupled to the sealed space.

18. The system of claim 17, wherein the angle is about 90°.

19. The system of claim 17, wherein the plurality of pores are configured to contract in a direction parallel to the first surface and the second surface.

20. The system of claim 17, wherein the sealing member is configured to be coupled to the second surface of the tissue interface with an adhesive.

21. The system of claim 17, wherein the sealing member comprises a polymer film.

22. The system of claim 17, wherein the tissue interface comprises a felted foam.

23. The system of claim 22, wherein the felted foam is felted to a firmness factor of 3 to 5.

24. The system of claim 22, wherein the felted foam has an uncompressed density of about 0.027 to about 0.034 g/cm³.

25. The system of claim 17, wherein the tissue interface has a thickness of about 5 mm to about 15 mm.

26. The system of claim 17, wherein the plurality of apertures are blind apertures.

27. The system of claim 26, wherein the plurality of apertures have a depth between about 5 mm to about 15 mm.

28. The system of claim 17, wherein the plurality of apertures extend through the thickness of the tissue interface from the first surface to the second surface.

\* \* \* \* \*